(12) United States Patent
Braun et al.

(10) Patent No.: US 10,799,627 B2
(45) Date of Patent: Oct. 13, 2020

(54) DEVICE AND METHOD FOR OPTIMIZING THE ENERGY CONSUMPTION IN A MEDICAL APPARATUS

(71) Applicant: Fresenius Medical Care Deutschland GmbH, Bad Homburg (DE)

(72) Inventors: Christian Braun, Edesheim (DE); Marco Graefe, Bad Homburg (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 1304 days.

(21) Appl. No.: 14/891,701

(22) PCT Filed: May 14, 2014

(86) PCT No.: PCT/EP2014/059820
§ 371 (c)(1),
(2) Date: Nov. 17, 2015

(87) PCT Pub. No.: WO2014/184227
PCT Pub. Date: Nov. 20, 2014

(65) Prior Publication Data
US 2016/0110508 A1    Apr. 21, 2016

(30) Foreign Application Priority Data
May 17, 2013   (EP) .................................... 13002607

(51) Int. Cl.
*A61M 1/16*     (2006.01)
*G16H 40/20*    (2018.01)

(52) U.S. Cl.
CPC .......... *A61M 1/1656* (2013.01); *A61M 1/166* (2014.02); *G16H 40/20* (2018.01);
(Continued)

(58) Field of Classification Search
CPC .............. A61M 1/1656; A61M 1/1686; A61M 2205/3561; A61M 2205/3666; A61M 1/166; G16H 40/20
(Continued)

(56) References Cited

U.S. PATENT DOCUMENTS 3,809,241 A     5/1974   Alvin
5,624,572 A *   4/1997   Larson .................... A61M 1/16
                                                                210/149
(Continued)

FOREIGN PATENT DOCUMENTS

CN       101184517       5/2008
CN       102123748       7/2011
(Continued)

*Primary Examiner* — Joy Chng
(74) *Attorney, Agent, or Firm* — Jackson Holman, PLLC

(57) ABSTRACT

A method associated with a system having a medical device that consumes energy during operation and an additional energy consumer is directed to optimizing energy consumption. The method includes providing a treatment plan information, which predetermines a temporal sequence for using the medical device, providing interaction information, which predetermines an interaction between the use of the medical device and the additional energy consumer, and providing control information for actuating the additional energy consumer based on the treatment plan information and the interaction information, so as to optimize the energy consumption of the system.

21 Claims, 2 Drawing Sheets

(52) U.S. Cl.
CPC ... *A61M 1/1686* (2013.01); *A61M 2205/3561* (2013.01); *A61M 2205/3666* (2013.01)

(58) Field of Classification Search
USPC ........................................................ 705/2–3
See application file for complete search history.

(56) References Cited

U.S. PATENT DOCUMENTS

| | | | |
|---|---|---|---|
| 7,749,393 | B2 | 7/2010 | Brugger et al. |
| 7,976,711 | B2 * | 7/2011 | Brugger .............. A61M 1/1656 210/767 |
| 2009/0206023 | A1 | 8/2009 | Rohde et al. |
| 2009/0211975 | A1 | 8/2009 | Brugger et al. |
| 2011/0192796 | A1 | 8/2011 | Smejtek et al. |
| 2012/0308431 | A1 * | 12/2012 | Kotsos ................ A61M 1/1686 422/3 |

FOREIGN PATENT DOCUMENTS

| | | |
|---|---|---|
| CN | 102325555 | 1/2012 |
| EP | 0436855 | 7/1991 |

* cited by examiner

DEVICE AND METHOD FOR OPTIMIZING THE ENERGY CONSUMPTION IN A MEDICAL APPARATUS

BACKGROUND OF THE INVENTION

1. Field of the Invention

The invention relates to the field of optimization of energy consumption in a medical facility, in particular optimization of energy consumption in a dialysis clinic.

2. Description of Related Art

The operation of medical facilities requires a supply of energy resources such as heat and electric power for operation of the medical devices themselves, on the one hand, for preparation for operation of the medical devices, on the other hand, and for providing substances needed in operation of the medical devices as well as for preparation of the devices used for this purpose. Operation of dialysis machines in a dialysis clinic is thus associated with consumption of electric power for operation of the dialysis machines but also consumption of heat and electric power for preparation of the dialysis machines, for example, for disinfection. Supplying dialysis fluid is associated with the consumption of electric power and heat for supplying dialysis fluid, including the starting materials for the dialysis fluid, such as ultrapure water, which is also referred to as permeate or RO water and is obtained by reverse osmosis (RO). The preparation of RO systems for operation includes disinfection with hot water or some other hot disinfectant combined with a corresponding consumption of heat or electric power.

Medical facilities must meet requirements with regard to achieving environmental goals and expenditures for their operation.

The object of the present invention is therefore to make available a method for optimizing energy consumption in a medical facility and a corresponding system.

SUMMARY OF THE INVENTION

This object is achieved by a method for optimizing energy consumption in a medical facility, and by a system for optimizing energy consumption in a medical facility, as described herein.

Advantageous embodiments of the invention are as described herein.

In accordance with the teaching of the present invention, a system for optimizing energy consumption by a medical facility with a medical machine and additional energy consumer is made available. The system comprises the following:

a clinical information system for supplying treatment planning information, which specifies a chronological sequence for use of the medical machine, a database for supplying interaction information that stipulates an interaction between the use of the medical machine and he additional energy consumer as well as a processing unit, which is connected to the clinical information system, and to the database and is adapted to supplying control information for activation of the additional energy consumer on the basis of the treatment planning information and the interaction information.

In one embodiment, the medical device is a dialysis machine, which constitutes a heat source during operation, and the additional energy consumer is a heating system. The interaction information in this embodiment comprises information about the heat production associated with operation of the dialysis machine. The control information for the heating in This embodiment is supplied taking into account treatment planning information for the dialysis machine and taking into account the information about heat Production by the dialysis machine. Thus, for example, at a certain point in time, which is determined from the treatment planning information, the heating may be lowered by an amount that corresponds to the data on the heat production associated with the operation of the dialysis machine.

In another embodiment, the medical device is a dialysis machine, and the additional energy consumer is a heat disinfection system for heat disinfection of a system for supplying RO water for the supply of dialysis fluid. The treatment planning information in this case indicates a period of time, by which the heat disinfection of the dialysis treatment must proceed. The control information for the heat disinfection system in this embodiment is supplied by taking into account treatment planning information for the dialysis machine and taking into account the data on the period of time by which the heat disinfection precedes the treatment. Thus, for example, operation of the heat disinfection system may be started at a certain point in time, which is determined from the treatment planning information and the stated period of time.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
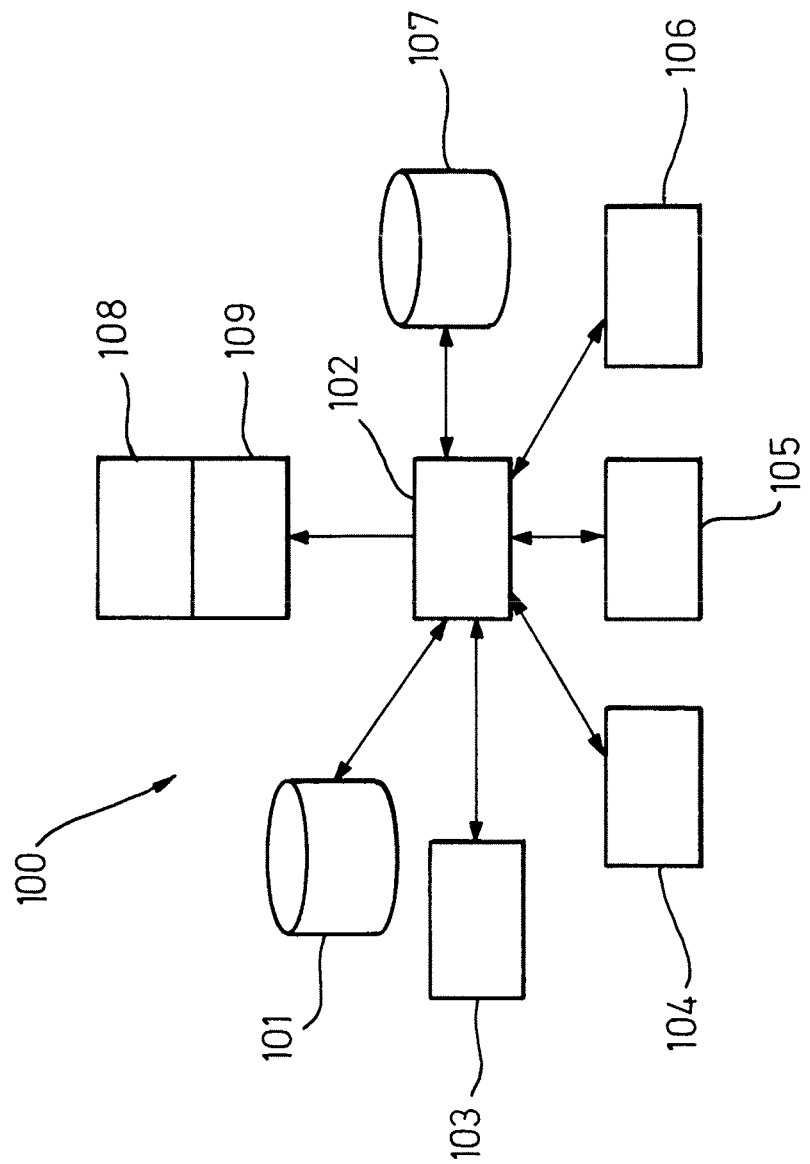
FIG. 1 shows a system for optimizing energy consumption in a medical facility.

FIG. 1 shows a system 100 for optimizing resource consumption and/or energy consumption in a medical facility, preferably in a dialysis clinic, in which medical devices including dialysis machines are operated. Furthermore, other energy consumers are also present in the medical facility, such as heating systems, disinfection systems for reverse osmosis systems, and reverse osmosis systems that supply ultrapure water as a starting substance for dialysis fluid by reverse osmosis.

The system 100 comprises a processing unit 102 for supplying control information for the medical devices and for the other energy consumers inside the dialysis clinic, in particular the heating systems and the disinfection systems.

Features of the medical devices including the dialysis machines that are associated with energy or resource management, such as heat consumption, electric power consumption, dissipation of heat or water consumption, are stored in the register 103.

Parameters based on the building service engineering, including an annual heating curve or annual energy consumption, are stored in the register 104.

Parameters pertaining to the various resource suppliers of the dialysis clinic are stored in the register 105, for example, including the annual heating curve of the heat supplier or the daily curve of an energy consumer of an energy supplier, including energy consumption prices that depend on the time of the day.

Curves of consumption within the medical facility and used on the medical facility are stored in the register 106, for example, consumption curves measured in the medical facility over a certain period of time for the consumption of electric power, water and/or heating energy.

The information managed in registers 103, 104, 105 and 106 relates to an interaction between use of the medical devices, including the dialysis machines, and other energy consumers inside the dialysis clinic.

Planning information, including occupancy plans for the use of dialysis machines by patients, treatment information as well as shift information pertaining to shift schedules is stored in the clinical information system 107. Treatment planning information includes time information about which times are scheduled for treatment of a certain patient with a certain machine.

The database 101 is used to manage the medical devices, including the dialysis machines.

The processing unit 102 can access the treatment planning information of the clinical information system 107 as well as the registers 103, 104, 105 and 106.

Based on the treatment planning information of the clinical information system and based on the interaction information, setting an interaction between the use of the medical device and the additional energy consumer, the processing unit 102 compiles control information or recommended settings 109 for medical devices, including dialysis machines, as well as the control information or recommended settings 108 for additional consumers for optimization of resource consumption, including water consumption and consumption of heating energy or electric power.

Figure 2:
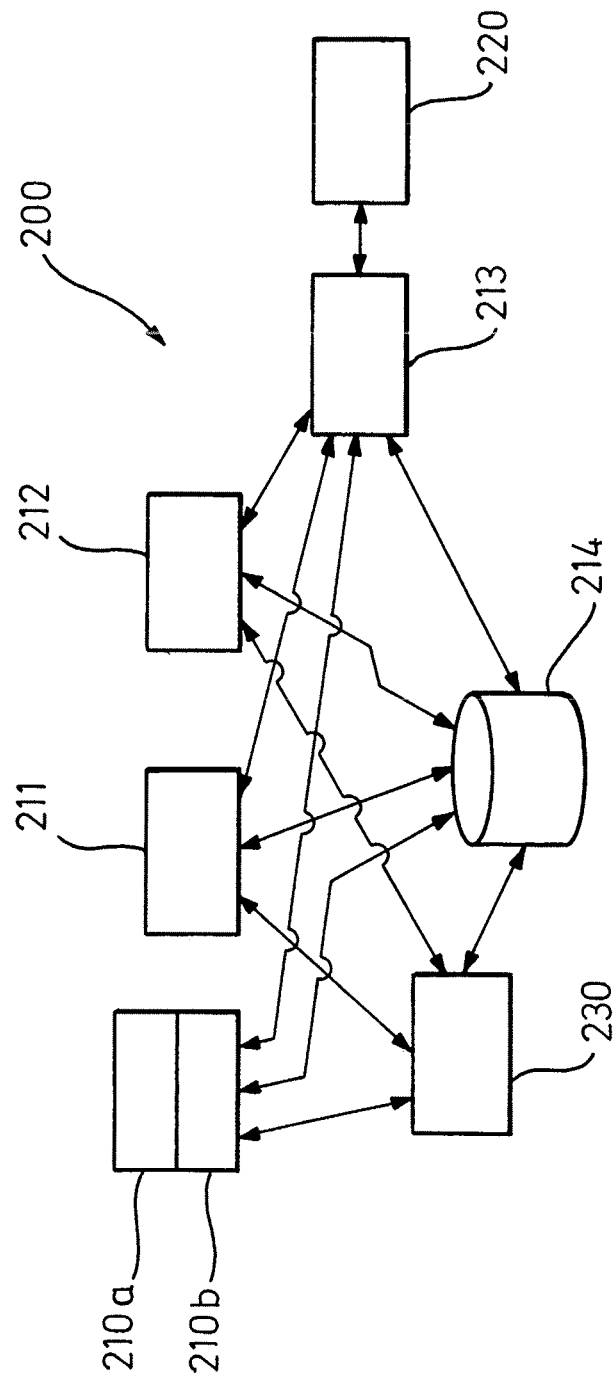
FIG. 2 shows another system for optimizing energy consumption in a medical facility.

FIG. 2 shows another system 200 for optimizing energy consumption in a medical facility.

The system 200 has medical devices 211, including dialysis machines, the operation of which is associated with the consumption of resources and energy, including electric power and/or heating energy.

The dialysis clinic also has building service engineering 212, which supplies resources for operation of the medical facility and is connected to other consumers of resources, including water, electric power and heating energy.

The additional consumers are equipped with actuators 210a and sensors 210b, where the sensors detect actual states of resource consumption by the consumers, including the prevailing water consumption, the prevailing electric power consumption and/or the prevailing thermal energy consumption. The sensors 210b control the consumers and specify the target values for consumption of resources, including a target value for water consumption, a target value for consumption of electric power and/or a target value for consumption of thermal energy.

So-called middleware 213 is connected to the actuators 210a, the sensors 210b, the medical devices 211, the building service engineering 212 and a control panel 220. The middleware serves to make an adjustment between data formats of the control panel 220, on the one hand, and the data formats of the actuators 210a, the sensors 210b, the medical devices 211 and the building service engineering 212, on the other hand. The connection of the middleware 213 to the actuators 210a and the sensors 210b, to the medical devices 211 and to the building service engineering 212 can be accomplished by means of a LAN (local area network) or a W-LAN (wireless local area network).

Interaction information, which sets the interaction between the consumption of resources by a certain medical device and a certain additional consumer, is stored in the database 214.

The database 214 is connected by data links to the medical devices 211 and the building service engineering 212 and to the actuators 210a and the sensors 210b. The database can also be operated outside of the medical facility. In this case, these data links may include an Internet connection, a connection via a mobile radio network or an M2M (machine-to-machine) connection.

The control panel 220 may be a control panel inside the medical facility or in an alternative embodiment, a central control panel 230 may be provided, executing corresponding functions, wherein the control panel preferably serves as a nation-wide control panel or as a control panel for medical facilities in various countries.

The invention being thus described, it will be apparent that the same may be varied in many ways. Such variations are not to be regarded as a departure from the spirit and scope of the invention, and all such modifications as would be recognized by one skilled in the art are intend to be included within the scope of the following claims.

What is claimed is:

1. A method of optimizing the energy consumption of a medical facility having a medical device that consumes energy during operation and an additional energy consumer, said method comprising the following steps:
   supplying treatment planning information specifying a chronological sequence for use of the medical device;
   supplying interaction from a database that specifies an interaction between the use of the medical device and the additional energy consumer, and a processing units;
   supplying control information based on the treatment planning information and the interaction information; and
   with the processing unit and the supplied control information, controlling operation of the medical device and controlling operation of the additional energy consumer so as to optimize the energy consumption of the medical facility.

2. The method according to claim 1, wherein the medical device during operation is a heat source, the additional energy consumer is a heater, and the interaction information includes heat production associated with operation of the medical device.

3. The method according to claim 1, wherein the additional energy consumer is a consumer of electric power, and the interaction information includes a consumption of electric power associated with operation of the medical device.

4. The method according to claim 3, wherein the interaction information includes a time-dependent specification for the consumption of electric power.

5. The method according to claim 4, wherein the time-dependent specification is for a total consumption of electric power or a price for electric power for the medical facility.

6. The method according to claim 1, wherein the additional energy consumer is an auxiliary device for operation of the medical device, and wherein the interaction information includes a chronological specification for the auxiliary device with respect to the treatment sequence.

7. The method according to claim 1, wherein the interaction information specifies a chronological reference between the operation of the medical device and operation of the additional energy consumer.

8. The method according to claim 1, wherein the medical device is a dialysis machine.

9. The method according to claim 8, wherein the additional energy consumer is a reverse osmosis unit apparatus for supplying a starting liquid, and wherein the control information is based on operation of the reverse osmosis system.

10. The method according to claim 9, wherein the reverse osmosis apparatus includes a disinfection unit, and wherein the control information is based on operation of the disinfection unit.

11. The method according to claim 9, wherein the additional energy consumer is a reverse osmosis unit apparatus for supplying permeate for preparation of dialysis fluid, and wherein the control information is based on disinfection of a permeate line of the reverse osmosis apparatus.

12. The method according to claim 1, wherein the control information is displayed on a display device.

13. The method according to claim 12, wherein the control information is displayed as an activation recommendation on a display screen.

14. The method according to claim 1, wherein the additional energy consumer is activated directly by using the control information.

15. A system for optimizing the energy consumption of a medical facility having a medical device that consumes energy during operation and an additional energy consumer, said system comprising:
 a clinical information system for supplying treatment information specifying a chronological sequence for use of the medical device;
 a database for supplying interaction information, specifying an interaction between the use of the medical device and the additional energy consumer; and
 a processing unit that is connected to the clinical information system and to the database, and is configured to supply control information for activating the additional energy consumer based on the treatment information and the interaction information,
 with the system being configured to employ the processing unit and the supplied control information to control operation of the medical device and the additional energy consumer so as to optimize the energy consumption of the medical facility.

16. The system according to claim 15, wherein the medical device during operation is a heat source, the additional energy consumer is a heater, and the interaction information includes heat production associated with operation of the medical device.

17. The system according to claim 15, wherein the additional energy consumer is a consumer of electric power and the interaction information includes a consumption of electric power associated with operation of the medical device.

18. The system according to claim 17, wherein the interaction information includes a time-dependent specification for the consumption of electric power.

19. The system according to claim 18, wherein the time-dependent specification is for a total consumption of electric power or a price for electric power for the medical facility.

20. The system according to claim 15, wherein the interaction information specifies a chronological reference between the operation of the medical device and operation of the additional energy consumer.

21. The system according to claim 15, wherein the medical device is a dialysis machine.

\* \* \* \* \*